(12) United States Patent
Maegawa et al.

(10) Patent No.: US 11,365,279 B2
(45) Date of Patent: Jun. 21, 2022

(54) FLUORESCENT RESIN COMPOSITION, MOLDED OBJECT AND MEDICAL DEVICE, AND METHOD FOR PRODUCING FLUORESCENT RESIN COMPOSITION

(71) Applicants: Public University Corporation Yokohama City University, Yokohama (JP); TRS Co., Ltd., Koshigaya (JP)

(72) Inventors: Jiro Maegawa, Yokohama (JP); Teruo Hashimoto, Koshigaya (JP); Koji Hirai, Okayama (JP)

(73) Assignees: PUBLIC UNIVERSITY CORPORATION YOKOHAMA CITY UNIVERSITY, Yokohama (JP); TRS Co., Ltd., Koshigaya (JP)

( * ) Notice: Subject to any disclaimer, the term of this patent is extended or adjusted under 35 U.S.C. 154(b) by 866 days.

(21) Appl. No.: 16/308,148

(22) PCT Filed: Nov. 13, 2017

(86) PCT No.: PCT/JP2017/040784
§ 371 (c)(1),
(2) Date: Dec. 7, 2018

(87) PCT Pub. No.: WO2018/123300
PCT Pub. Date: Jul. 5, 2018

(65) Prior Publication Data
US 2019/0144594 A1 May 16, 2019

(30) Foreign Application Priority Data
Dec. 26, 2016 (JP) .............................. JP2016-250876

(51) Int. Cl.
*C08G 18/38* (2006.01)
*A61L 29/06* (2006.01)
(Continued)

(52) U.S. Cl.
CPC .......... *C08G 18/3857* (2013.01); *A61L 29/06* (2013.01); *A61L 31/06* (2013.01);
(Continued)

(58) Field of Classification Search
CPC .... C08G 18/3857; C08G 18/00; C08G 18/10; C08G 18/38; C08G 18/44; C08G 18/64;
(Continued)

(56) References Cited

U.S. PATENT DOCUMENTS

2012/0225256 A1   9/2012   Sugasaki
2012/0238701 A1*  9/2012   Yamada ................. C08G 18/12
                                                           524/839
(Continued)

FOREIGN PATENT DOCUMENTS

EP   2980160 A1   2/2016
JP   3294334 A    12/1991
(Continued)

*Primary Examiner* — Andrew J. Oyer
(74) *Attorney, Agent, or Firm* — The Webb Law Firm

(57) ABSTRACT

A fluorescent resin composition including a urethane resin which is a polymer having at least a polyol compound (A), a polyisocyanate compound (B) and a chain-extending compound (C) as structural units, and a fluorescent dye that emits fluorescence by undergoing irradiation with near infrared light within a wavelength region of 700 nm to 1300 nm, the polyol compound (A) being an aliphatic polycarbonate diol (A1). In addition, a molded object made of the above-described fluorescent resin composition, and also a medical device including the molded object. Examples of the medical device can include a wire for detecting the position of a lymph vessel that includes the molded object made of the fluorescent resin composition as a fluorescent marker.

13 Claims, 3 Drawing Sheets

(51) Int. Cl.

| | |
|---|---|
| *A61L 31/06* | (2006.01) |
| *A61M 25/09* | (2006.01) |
| *C08G 18/10* | (2006.01) |
| *C08L 75/04* | (2006.01) |
| *C08G 18/64* | (2006.01) |
| *C08K 5/42* | (2006.01) |
| *C08L 75/06* | (2006.01) |
| *C08G 18/00* | (2006.01) |
| *C08G 18/76* | (2006.01) |
| *C08G 18/75* | (2006.01) |
| *C08G 18/44* | (2006.01) |
| *C08K 5/00* | (2006.01) |
| *C09B 23/01* | (2006.01) |

(52) U.S. Cl.
CPC .............. *A61M 25/09* (2013.01); *C08G 18/00* (2013.01); *C08G 18/10* (2013.01); *C08G 18/38* (2013.01); *C08G 18/44* (2013.01); *C08G 18/64* (2013.01); *C08G 18/755* (2013.01); *C08G 18/7671* (2013.01); *C08K 5/0041* (2013.01); *C08K 5/42* (2013.01); *C08L 75/04* (2013.01); *C08L 75/06* (2013.01); *C09B 23/0041* (2013.01); *C08L 2203/02* (2013.01)

(58) Field of Classification Search
CPC ... C08G 18/755; C08G 18/7671; A61L 29/06; A61L 31/06; A61M 25/09; C08K 5/0041; C08K 5/42; C08L 75/04; C08L 75/06; C08L 2203/02; C09B 23/0041
See application file for complete search history.

(56) References Cited

U.S. PATENT DOCUMENTS

| | | |
|---|---|---|
| 2013/0274401 A1 | 10/2013 | Allen et al. |
| 2013/0284040 A1 | 10/2013 | Sugasaki |
| 2015/0152287 A1 | 6/2015 | Flosbach et al. |
| 2015/0182673 A1* | 7/2015 | Delaney, Jr. ............ A61L 31/14 525/123 |
| 2015/0357554 A1 | 12/2015 | Krause et al. |
| 2016/0053146 A1 | 2/2016 | Miyake et al. |

FOREIGN PATENT DOCUMENTS

| | | |
|---|---|---|
| JP | 2004276278 A | 10/2004 |
| JP | 2007334325 A | 12/2007 |
| JP | 200986350 A | 4/2009 |
| JP | 201171387 A | 4/2011 |
| JP | 2011110393 A | 6/2011 |
| JP | 2011147580 A | 8/2011 |
| JP | 2011178963 A | 9/2011 |
| JP | 2012183712 A | 9/2012 |
| JP | 2013240998 A | 12/2013 |
| JP | 2014136114 A | 7/2014 |
| JP | 2014136115 A | 7/2014 |
| JP | 2014136116 A | 7/2014 |
| JP | 2014155510 A | 8/2014 |
| JP | 2015514848 A | 5/2015 |
| JP | 2015533671 A | 11/2015 |
| WO | 2006043569 A1 | 4/2006 |
| WO | 2009145242 A1 | 12/2009 |
| WO | 2010007876 A1 | 1/2010 |
| WO | 2011058937 A1 | 5/2011 |
| WO | 2013146354 A1 | 10/2013 |
| WO | 2014156423 A1 | 10/2014 |
| WO | 2015046369 A1 | 4/2015 |
| WO | 2016120406 A1 | 8/2016 |

* cited by examiner

FLUORESCENT RESIN COMPOSITION, MOLDED OBJECT AND MEDICAL DEVICE, AND METHOD FOR PRODUCING FLUORESCENT RESIN COMPOSITION

CROSS-REFERENCE TO RELATED APPLICATIONS

This application is the United States national phase of International Application No. PCT/JP2017/040784 filed Nov. 13, 2017, and claims priority to Japanese Patent Application No. 2016-250876 filed Dec. 26, 2016, the disclosures of which are hereby incorporated in their entirety by reference.

TECHNICAL FIELD

The present invention relates to a fluorescent resin composition, molded object and medical device which emit fluorescence by undergoing irradiation with near infrared light, and a method for producing the fluorescent resin composition.

BACKGROUND ART

Techniques for performing medical diagnosis and surgical operation are known including administering into a living body a fluorescent dye (near infrared fluorescent dye) which excites by undergoing irradiation with near infrared rays to emit near infrared fluorescence, and observing the fluorescence through the surface of the living body. As the fluorescent dye, indocyanine green (hereinafter, also referred to as "ICG") having high light transmittance through a living tissue and high safety to a living body has been used. ICG is used as test agents for liver function and circulatory function. In addition, utilizing such high light transmittance of ICG through a living tissue, medical diagnosis, surgical operation, etc. have been conducted including locally administering ICG into a body, for example to the site of blood vessel, lymph vessel, brain, eye, stomach, breast, esophagus, or skin, and observing the near infrared fluorescent light from ICG.

Furthermore, a medical device has been developed in which a marker portion for confirming the position of the medical device in a living body is formed by applying a fluorescent dye to the surface of the medical device, or kneading it in a resin for use in the medical device such as catheter or guide wire.

In order to achieve the above, a technique is required for enclosing the fluorescent dye used for the marker portion in the resin so as not to dissolve into an aqueous phase such as blood or lymph. For example, Patent Literature 1 discloses a guide wire whose marker portion includes water-soluble indocyanine green (claim 3). However, this Literature does not disclose via what kind of material (carrier) the surface of the guide wire is coated with indocyanine green.

Patent Literature 2 discloses a ureteral catheter having one or more lumens including a near infrared fluorescent dye that emits near infrared fluorescence upon irradiation with near infrared rays having wavelengths of 500 nm to 1400 nm (claim 1). In this Literature, indocyanine green is exemplified as the near infrared fluorescent dye (paragraph 0024). In addition, as a method for introducing the near infrared fluorescent dye to a part or whole of the ureteral catheter, a method is disclosed including preparing a polymer composition by kneading a solid or melt of a polymer as a raw material with the near infrared fluorescent dye, and manufacturing the catheter using this polymer composition (paragraph 0061), and thermoplastic polyurethane and the like are exemplified as the polymer for use (paragraph 0062).

Patent Literature 3 discloses a biliary catheter having a lumen including a near infrared fluorescent dye that emits near infrared fluorescence upon irradiation with near infrared rays having wavelengths of 500 nm to 1400 nm (claim 1). In addition, Patent Literature 4 discloses a sheath introducer for artery in which a conductor portion of a sheath includes a near infrared fluorescent dye that emits near infrared fluorescence upon irradiation with near infrared rays having wavelengths of 500 nm to 1400 nm (claim 1). Furthermore, Patent Literature 5 discloses an indwelling needle in which a conductor portion of a sheath includes a near infrared fluorescent dye that emits near infrared fluorescence upon irradiation with near infrared rays having wavelengths of 500 nm to 1400 nm (claim 1). Similarly to Patent Literature 1, these Literatures also exemplify indocyanine green as the near infrared fluorescent dye, and polyurethane etc. as a material to be kneaded with the dye.

Furthermore, one of the inventors of the present application has previously disclosed in Patent Literature 6 a medical device in which the surface of the base material constituting the medical device is coated with a primer resin, and the primer resin is coated with a hydrophilic polymer (claim 1). This Literature discloses that this primer resin is a polyurethane urea resin obtained by copolymerizing a high-molecular diol, diisocyanate, and low-molecular weight compound, the high-molecular diol is a polycarbonate diol having a molecular weight of 600 or more (claim 5), particularly preferably an aliphatic polycarbonate diol having 5 or more carbon atoms (paragraph 0013).

CITATION LIST

Patent Literature

Patent Literature 1: JP 2011-147580 A
Patent Literature 2: JP 2014-136116 A
Patent Literature 3: JP 2014-155510 A
Patent Literature 4: JP 2014-136114 A
Patent Literature 5: JP 2014-136115 A
Patent Literature 6: JP 2011-110393 A

SUMMARY OF INVENTION

Technical Problem

Patent Literatures 2 to 5 disclose a fluorescent resin composition in which a fluorescent dye and a urethane resin are kneaded, but do not specifically disclose what type of polyurethane is used.

Generally, as a high-molecular polyol in a urethane resin used in a medical field or the like, a polyether polyol and polyester polyol are known. However, when these high molecular weight polyols are used in a urethane resin, a fluorescent dye tends to dissolve from the urethane resin, and also a fluorescent dye is difficult to disperse in the urethane resin. Therefore, the fluorescent dye aggregates, and thus the emission intensity tends to become poorer.

In particular, indocyanine green has a hydrophobic structure in which the conjugated system of a green chromophore and near infrared fluorophore is long. Therefore, when mixed in the above-described conventional urethane resin, the fluorescent dye tends to precipitate on the surface of the urethane resin to dissolve into water, and the fluorescent dye tends to aggregate, leading to low dispersibility in the urethane resin and low fluorescent luminance.

Furthermore, indocyanine green exhibits water solubility because the molecule has a sulfonic acid group bonded. Accordingly, when applied to the surface of a medical device, indocyanine green will dissolve into an aqueous phase such as blood and lymph, and spread over and attach to the whole lipid in a non-targeted living tissue. As a result, indocyanine green cannot be easily removed. Therefore, it is difficult to confirm the position of the medical device, which may interfere with medical cares.

On the other hand, Patent Literature 6 discloses, as a material suitable for coating a hydrophilic polymer, a urethane urea resin in which an aliphatic polycarbonate diol having 5 or more carbon atoms is used as a high-molecular diol. However, this Literature does not disclose a fluorescent resin composition in which a fluorescent dye is kneaded with a urethane urea resin, much less dissolution, dispersibility or the like of a fluorescent dye at all.

In view of the above-described problems, it is an object of the present invention to provide a fluorescent resin composition from which a fluorescent dye is hardly dissolved into water and in which the fluorescent dye has high dispersibility in a resin, a molded object and a medical device using the fluorescent resin composition, as well as a method for producing the fluorescent resin composition.

Solution to Problem

The inventors of the present invention conducted intensive studies to achieve the above object. As a result, it has found that a fluorescent resin composition in which a fluorescent dye that emits fluorescence upon irradiation with near infrared light is mixed with a urethane resin having an aliphatic polycarbonate diol as a structural unit reduces dissolution of the fluorescent dye into water, and is excellent in dispersibility of the fluorescent dye into the resin. Accordingly, the present invention has been completed.

That is, a fluorescent resin composition according to the present invention is characterized by containing a urethane resin which is a polymer having at least a polyol compound (A), a polyisocyanate compound (B) and a chain-extending compound (C) as structural units, and a fluorescent dye that emits fluorescence by undergoing irradiation with near infrared light within a wavelength region of 700 nm to 1300 nm, the polyol compound (A) being an aliphatic polycarbonate diol (A1).

In this case, the polyol compound (A) preferably has a number average molecular weight within a range of 500 to 5000.

It is also preferable that the polyisocyanate compound (B) is one or more selected from an alicyclic diisocyanate (B1), aliphatic diisocyanate (B2) and aromatic diisocyanate (B3).

Furthermore, it is preferable that the urethane resin is a urethane urea resin, and the chain-extending compound (C) further contains one or more diamine compounds (C1) selected from an alicyclic diamine (C1-1) and aliphatic diamine (C1-2) as a structural unit.

In particular, it is preferable that the molar ratio of the polyol compound (A), the polyisocyanate compound (B) and the chain-extending compound (C) constituting the urethane resin satisfies C/(B−A)>1.0.

In addition, it is preferable that the urethane resin is bonded to a silane coupling compound (D) having an amino group.

In particular, it is preferable that the molar ratio of the polyol compound (A), the polyisocyanate compound (B), the chain-extending compound (C) and the silane coupling compound (D) constituting the urethane resin satisfies C/(B−A−D)>1.0.

In the above case, it is preferable that the fluorescent dye is a cyanine dye that emits fluorescence by undergoing irradiation with near infrared light within a wavelength region of 700 nm to 900 nm.

In particular, it is preferable that the cyanine dye is indocyanine green or a derivative thereof.

In addition, the present invention is a molded object characterized by including the fluorescent resin composition according to any one of the above.

Furthermore, the present invention is a medical device characterized by including the molded object.

In this case, it is preferable that the medical device is a medical wire including the molded object as a fluorescent marker.

In addition, the present invention is a method for producing a fluorescent resin composition, characterized by including a solution preparing step of polymerizing at least a polyol compound (A), a polyisocyanate compound (B) and a chain-extending compound (C) in the presence of a solvent to prepare a solution of a urethane resin, and a dye mixing step of mixing a fluorescent dye that emits fluorescence by undergoing irradiation with near infrared light within a wavelength region of 700 nm to 1300 nm with the solution of the urethane resin, the polyol compound (A) being an aliphatic polycarbonate diol (A1).

In this case, it is preferable that the solution preparing step includes a step of reacting the polyol compound (A) with the polyisocyanate compound (B) to prepare a prepolymer solution, and a urethane polymerizing step of adding the chain-extending compound (C) to the prepolymer solution to prepare the urethane resin.

Furthermore, it is preferable that the solution preparing step further includes a step of dissolving a silane coupling compound (D) in a solvent.

In accordance with the present invention, a fluorescent resin composition from which a fluorescent dye is hardly dissolved into water and in which the fluorescent dye has high dispersibility in a resin, a molded object and a medical device using the same, as well as a method for producing the fluorescent resin composition can be provided.

DESCRIPTION OF THE INVENTION

1. Fluorescent Resin Composition

Figure 1A:
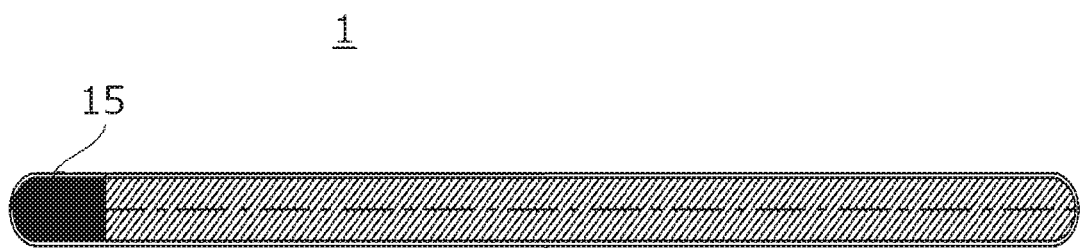
FIG. 1A is schematic side view of a wire for detecting the position of a lymph vessel according to one embodiment of the present invention.

A fluorescent resin composition according to the present invention includes a urethane resin which is a polymer having at least a polyol compound (A) and a polyisocyanate compound (B) as structural units, and a fluorescent dye that emits fluorescence by undergoing irradiation with near infrared light within a wavelength region of 700 nm to 1300 nm.

(1) Urethane Resin

The urethane resin according to the present invention has at least a polyol compound (A), a polyisocyanate compound (B), and a chain-extending compound (C) as structural units. Here, the "structural unit" means a basic unit constituting the main chain of the urethane resin. The urethane resin may be a polyurethane resin or a polyurethane urea resin. The polyurethane resin has a urethane bond in the molecule. The polyurethane urea resin has urethane bond and urea bond in the molecule, and an amino group at the end of the molecule. From the viewpoint of compatibility with a fluorescent dye, a polyurethane urea resin is more preferable as the urethane resin.

(A) Polyol Compound (Aliphatic Polycarbonate Diol (A1))

The polyol compound (A) is a compound having two or more hydroxyl groups (—OH). The number average molecular weight of the polyol compound (A) is preferably 500 or more. From the viewpoints of water resistance and adhesiveness, a polycarbonate diol can be used as the polyol compound (A).

The polyol compound (A) of the present invention is an aliphatic polycarbonate diol (A1) obtained by polycondensation of an aliphatic diol (A1-1) having two hydroxyl groups and a carbonate compound (A1-2) as monomer units. As the aliphatic polycarbonate diol (A1), an aliphatic polycarbonate diol having as a structural unit an aliphatic diol having 4 or more carbon atoms is particularly preferable. It is not preferable that an alicyclic polycarbonate diol and aromatic polycarbonate diol are used as the polyol compound (A), because the urethane resin becomes too rigid and thus brittle, and becomes easy to peel off from the base material when it is used as a coating film. The upper limit of the number of carbon atoms in the aliphatic diol is not particularly limited, but the number of carbon atoms is preferably 15 or less, more preferably 10 or less. The number average molecular weight of the aliphatic polycarbonate diol (A1) is preferably within a range of 500 to 5000, more preferably within a range of 1000 to 4000. Furthermore, it is particularly preferably within a range of 1500 to 3000. When the number average molecular weight is less than 500, the urethane resin tends to become so brittle that the dissolution property of fluorescent dye tends to be larger. On the other hand, when the number average molecular weight exceeds 5000, the urethane resin tends to become too soft, and polymerization of the urethane resin tends to be difficult. The number average molecular weight can be determined through measurement by a terminal group determination method.

The aliphatic diol (A1-1) having 4 or more carbon atoms can include a compound represented by following Formula (1).

[Formula 1]

(wherein $R_1$ is a linear or branched alkylene group having 4 to 15 carbon atoms.)

From the viewpoints of water resistance, lubrication durability and flexibility, examples of the aliphatic diol (A1-1) having 4 or more carbon atoms including 1,4-butanediol, 1,5-pentamethylenediol, 1,6-hexanediol, neopentyl glycol, 3-methyl-1,5-pentanediol, 1,6-hexamethylenediol, 1,8-octamethylenediol, 2-ethyl hexamethylenediol, nonamethylenediol and 2-methyloctamethylenediol can be suitably used. One kind of these aliphatic diols (A1-1) may be used alone, or two or more kinds thereof may be used.

The carbonate compound (A1-2) constituting the aliphatic polycarbonate diol (A1) is not particularly limited, and examples thereof include dialkyl carbonate, alkylene carbonate and diaryl carbonate.

The carbonate compound (A1-2) can include a compound represented by following Formula (2).

[Formula 2]

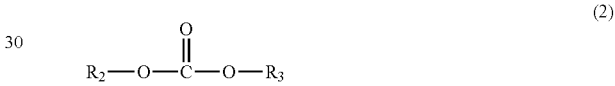

(wherein each $R_2$ and $R_3$ is an alkyl group such as methyl group, ethyl group and propyl group, or an aryl group, which may be the same as or different from each other, or $R_2$ and $R_3$ may be bonded to each other to form a hydrocarbon ring having 2 to 6 carbon atoms.)

Examples of the dialkyl carbonate can include a carbonate compound having an alkyl group having 1 to 3 carbon atoms, and specific examples thereof can include diethyl carbonate, dimethyl carbonate, ethyl methyl carbonate, methyl propyl carbonate, ethyl propyl carbonate and dipropyl carbonate. Examples of the alkylene carbonate can include a carbonate compound having an alkylene group having 2 to 3 carbon atoms, and specific examples thereof can include ethylene carbonate and propylene carbonate. Examples of the diaryl carbonate can include a carbonate compound having a phenyl group or biphenyl group, and specific examples thereof can include diphenyl carbonate. One kind of these carbonate compounds (A1-2) may be used alone, or two or more kinds thereof may be used.

Examples of the aliphatic polycarbonate diol (A1) obtained by polycondensation of the aliphatic diol (A1-1) having 5 or more carbon atoms and the carbonate compound (A1-2) can include a compound represented by following Formula (3).

[Formula 3]

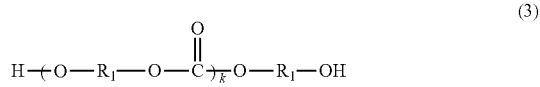

(wherein k is an integer of up to 45, and $R_1$ is a linear or branched alkylene group having 4 to 15 carbon atoms.)

The aliphatic polycarbonate diol (A1) can be obtained by polycondensation of the aliphatic diol (A1-1) and the carbonate compound (A1-2) using a publicly known method, for example, transesterification. The transesterification is preferably performed in the presence of a publicly known transesterification catalyst. Examples of the transesterification catalyst can include: compounds of Group 1 metal in the periodic table such as lithium, sodium, potassium, rubidium and cesium; compounds of Group 2 metal in the periodic table such as magnesium, calcium, strontium and barium; compounds of Group 4 metal in the periodic table such as titanium and zirconium; compounds of Group 5 metal in the periodic table such as hafnium; compounds of Group 9 metal in the periodic table such as cobalt; compounds of Group 12 metal in the periodic table such as zinc; compounds of Group 13 metal in the periodic table such as aluminum; compounds of Group 14 metal in the periodic table such as germanium, tin and lead; compounds of Group 15 metal in the periodic table such as antimony and bismuth; compounds of lanthanoid metal such as lanthanum, cerium, europium and ytterbium.

When the transesterification catalyst is added, the amount of transesterification catalyst added to the total charged amount is preferably 1 to 20000 ppm by weight, more preferably 10 to 5000 ppm by weight, particularly preferably 20 to 4000 ppm by weight.

The transesterification can be performed under a publicly known reaction condition. The reaction temperature is usually within a range of 10 to 200° C., preferably within a range of 50 to 150° C., although it depends on the condition for the used monomer, catalyst and the like. The reaction time is usually within a range of 10 minutes to 24 hours, preferably within a range of 1 to 10 hours.

In addition, when the transesterification catalyst remains in the polymerized polycarbonate diol, color tone change etc. of the urethane resin tends to occur. Therefore, after completion of the transesterification, it is preferable to add a catalyst deactivator for deactivating the transesterification catalyst to the reaction system to deactivate the transesterification catalyst. Examples of such a catalyst deactivator can include water and phosphorus compounds, with water being particularly preferred. Specific examples of the phosphorus compounds can include inorganic phosphoric acids such as phosphoric acid and phosphorous acid, and organophosphate esters such as dibutyl phosphate, tributyl phosphate, trioctyl phosphate, triphenyl phosphate and triphenyl phosphite.

(B) Polyisocyanate Compound

The polyisocyanate compound (B) is a compound having two or more isocyanate groups (—NCO). As the polyisocyanate compound, it is preferable to use one or more diisocyanate compounds selected from an alicyclic diisocyanate (B1), aliphatic diisocyanate (B2) and aromatic diisocyanate (B3). From the viewpoint of solubility in general solvents, an alicyclic diisocyanate (B1) or aliphatic diisocyanate (B2) is particularly preferable.

Examples of the alicyclic diisocyanate (B1) include isophorone diisocyanate and dicyclohexylmethane diisocyanate. Examples of the aliphatic diisocyanate (B2) include hexamethylene diisocyanate and nonamethylene diisocyanate. Further, examples of the aromatic diisocyanate (B3) include hydrogenated xylylene diisocyanate, diphenylmethane diisocyanate (MDI) and toluene diisocyanate (TDI).

(C) Chain-Extending Compound

The chain-extending compound (C) is a compound that will become a part of the constitutional unit of the main chain of the urethane resin of the present invention. As the chain-extending compound (C), a publicly known chain extender for production of ordinary polyurethane resins can be used. As the chain-extending compound (C), a low-molecular weight compound having in the molecule two or more active hydrogen atoms capable of reacting with an isocyanate group and having a molecular weight of 300 or less is preferable. As the chain-extending compound (C), a diamine compound (C1) or diol compound (C2) is more preferable.

(C1) Diamine Compound

The diamine compound (C1) can include one or more kinds of diamine compounds selected from an alicyclic diamine (C1-1) and aliphatic diamine (C1-2). Examples of the alicyclic diamine (C1-1) include isophorone diamine, dicyclohexylmethanediamine and hydrogenated xylylenediamine. Examples of the aliphatic diamine (C1-2) include ethylenediamine, propylenediamine, hexamethylenediamine and nonamethylenediamine. From the viewpoints of water resistance and lubrication durability, the diamine compound (C1) preferably has 6 or more carbon atoms.

It is also possible to use an aromatic diamine such as diphenylmethanediamine, xylylenediamine or toluenediamine in combination with the alicyclic diamine (C1) and aliphatic diamine (C2) within a range not to impair the solubility in a solvent. One kind of the diamine compounds (C1) may be used alone, or two or more kinds thereof may be used in combination.

When the chain-extending compound (C) is the diamine compound (C1), the urethane resin becomes a polyurethane urea resin. Because the polyurethane urea resin has an amino group at the end of the molecule, the intermolecular interaction with a fluorescent dye becomes so stronger that dissolution of the fluorescent dye into water, blood, lymph or the like can be further suppressed. Furthermore, the polyurethane urea resin has so high solubility in a low-boiling-point solvent and so high compatibility with a fluorescent dye that the dispersibility of fluorescent dye also increases, and a fluorescent dye can be suppressed from aggregating or precipitating (bleeding out) on the resin surface. In this way, using the polyurethane urea resin allows the dispersibility of fluorescent dye to be so excellent that the emission intensity becomes higher upon irradiation with near infrared light, and thus higher-luminance fluorescence can be observed. In addition, the polyurethane urea resin is also so excellent in water resistance, light resistance and heat resistance that discoloration of fluorescent dye can be suppressed.

(C2) Diol Compound

In addition, the chain-extending compound (C) can have the diol compound (C2) as a further structural unit. Examples of the diol compound (C2) include alkylene glycols such as ethylene glycol, 1,4-butanediol, 1,3-butanediol, 1,2-butanediol, hexanediol and nonanediol. One kind of the chain-extending compounds (C) may be used alone, or two or more kinds thereof may be used in combination.

(X) Urethane Resin

A urethane resin (X) having an aliphatic polycarbonate diol (A1), a polyisocyanate compound (B) and a chain-extending compound (C) as structural units is a block polymer including at least these three components as structural components. The urethane resin (X) constitutes a molecular chain by combining blocks (repeating units) having different lengths as follows, for example.

-A-B-C-B-C-B-A-B-A-B-C-B-C-B-C-B-A-B-C-B-A-B-C-B-C-B-C-B-A- . . .

The urethane resin (X) can include a compound having a structure represented by following Formula (4).

-[-A-(-B-C-)m-B-]n-A-   Formula (4)

(wherein A is the above-described aliphatic polycarbonate diol (A1), B is the above-described polyisocyanate compound (B), C is the above-described chain-extending compound (C), m is an integer of 1 or more indicating the number of repeating units of "-B-C-", in which the "-B-C-" of one repeating unit may be the same as or different from the other(s), and n is an integer of 1 or more indicating the number of repeating units of "-A-(-B-C-)m-B-", in which the "-A-(-B-C-)m-B-" of one repeating unit may be the same as or different from the other(s).)

In the present invention, the polyol compound (A) constituting the urethane resin has the aliphatic polycarbonate diol (A1) as a structural unit. Because the aliphatic polycarbonate diol (A1) has a carbonate bond in the main chain, the intermolecular interaction with the polar group of a fluorescent dye so strongly occurs that the fluorescent resin composition of the present invention in which the urethane resin and a fluorescent dye are mixed makes it difficult for the fluorescent dye to dissolve from the resin into water. Furthermore, the aliphatic polycarbonate diol having an aliphatic diol having 4 or more carbon atoms as a structural unit has so strong hydrophobicity and so strong intermolecular cohesive force that entry of water into the urethane resin is extremely suppressed. Accordingly, it is difficult for a fluorescent dye to dissolve from the urethane resin. In addition, the urethane resin of the present invention has a polar group such as a urethane bond and carbonate bond, and intermolecular interaction with the polar group of a fluorescent dye occurs, so that the urethane resin is also excellent in dispersibility of the fluorescent dye. Therefore, the fluorescent resin composition of the present invention has excellent fluorescent luminance even in a system in which water is present.

On the other hand, it is not preferable that a polyetherdiol or polyesterdiol for use in a general urethane resin is used as the polyol compound (A), because a fluorescent dye is easy to dissolve and the dispersibility of fluorescent dye is poor.

(D) Silane Coupling Compound

Furthermore, the urethane resin according to the present invention may contain a silane coupling compound (D) having an amino group. The silane coupling compound (D) having an amino group may be one linked to the main chain of the urethane resin as a structural unit or may be one bonded to the side chain thereof. Examples of the silane coupling compound (D) having an amino group include 3-aminopropyltrimethoxysilane, 3-aminopropyltriethoxysilane, 3-phenylaminopropyltrimethoxysilane, 3-(2-aminoethyl) aminopropyl trimethoxysilane and 3-(2-aminoethyl) aminopropylmethyldimethoxysilane. Containing the silane coupling compound (D) having an amino group further improves the enclosing effect on a fluorescent dye and the adhesiveness to a base material such as metal. One kind of the silane coupling compounds (D) having an amino group may be used alone, or two or more kinds thereof may be used in combination.

The ratio of the polyol compound (A) to the polyisocyanate compound (B) contained in the urethane resin can be appropriately adjusted, but is usually within a range of 1:2 to 1:8 in molar ratio, preferably within a range of 1:2 to 1:6. When the molar ratio is 1:2 or more, the dissolution property of fluorescent dye tends to become large. On the other hand, when the molar ratio is 1:8 or less, the solution stability of urethane resin tends to deteriorate, and the dispersibility of fluorescent dye tends to decrease. In addition, the molar ratio of the polyol compound (A), polyisocyanate compound (B) and chain-extending compound (C) preferably satisfies C/(B−A)>1.0. Furthermore, when the urethane resin includes the silane coupling compound (D), the molar ratio of the polyol compound (A), polyisocyanate compound (B), chain-extending compound (C) and silane coupling compound (D) preferably satisfies C/(B−A−D)>1.0.

As described above, because the urethane resin according to the present invention has a carbonate bond in the polycarbonate diol, the intermolecular interaction with a fluorescent dye is so strong that the fluorescent dye is enclosed in the urethane resin. Accordingly, the fluorescent dye can be suppressed from dissolving into an aqueous phase. In addition, when the urethane resin is the polyurethane urea resin, because the polyurethane urea resin has an amino group at the end of the molecule, the intermolecular interaction and compatibility with a fluorescent dye are further improved so that dissolution of the fluorescent dye into an aqueous phase can be further suppressed.

(2) Fluorescent Dye

As the fluorescent dye according to the present invention, one which emits fluorescence by undergoing irradiation with near infrared light within a wavelength region of 700 nm to 1300 nm can be used. Here, the near infrared light within a wavelength region of 700 nm to 1300 nm means near infrared light having an arbitrary wavelength range within the wavelength region, and the arbitrary wavelength range means a part or all wavelength range within the above-described wavelength range. In addition, in the present application, the fluorescence means that a fluorescent dye is excited by undergoing irradiation with near infrared light and emits near infrared light having a wavelength different from (longer than) the wavelength of the irradiated near infrared light. Examples of such a fluorescent dye can include an azo-boron complex compound, hydrazone compound, cyanine compound, Patent blue and Indigo carmine.

As the fluorescent dye, from the viewpoint of transmittance through a living tissue, it is preferable to use a cyanine compound (cyanine dye) that emits near infrared fluorescence within a wavelength region of 700 nm to 900 nm. The cyanine dye is a dye having a heterocyclic ring including nitrogen at both ends of a polymethine skeleton, one nitrogen atom being ammonium having a cation structure, and the other nitrogen atom forming a tertiary amine structure. Such a structure can include a structure represented by following Formula (5).

[Formula 4]

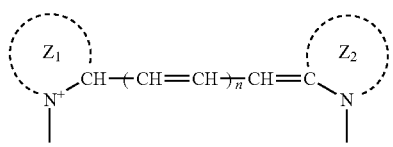

(5)

(wherein n is an integer of 1 to 5, and each $Z_1$ and $Z_2$ is a heterocyclic ring selected from the group consisting of indole, benzoxazole, benzothiazole, naphthothiazole and quinoline, which may be the same as or different from each other.)

Because the cyanine dye is water-soluble and thus difficult to accumulate in a living body, it is known to have high safety. As the cyanine dye, a publicly known cyanine dye can be used, and examples thereof can include compounds selected from the group consisting of 1,1',3,3,3',3'-hexamethylindotricarbocyanine iodide (2-[7(1,3-dihydro-1,3,3-trimethyl-2H-indole-2-indene)-1,3,5-heptatrienyl)]-1,3,3-trimethyl-3H-indolium iodide) and indocyanine green, and derivatives thereof. Among them, from the viewpoints of discharging property from a living body and safety, one having a sulfonic acid group is preferable, for example, indocyanine green (ICG) or a derivative thereof is particularly preferable.

Indocyanine green (ICG) is a compound represented by following Formula (6).

[Formula 5]

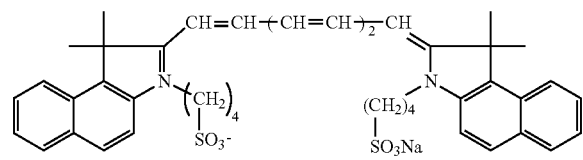

(6)

In addition, the derivative of indocyanine green (ICG) can include a compound represented by following Formula (7).

[Formula 6]

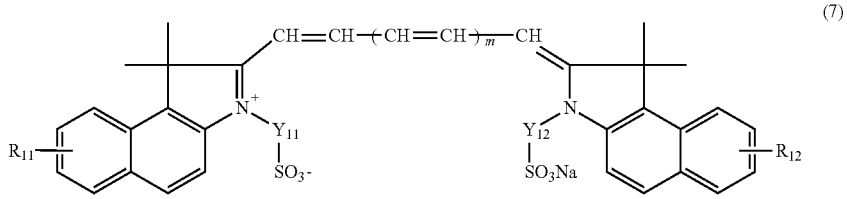

(7)

(wherein m is an integer of 1 to 3, each $Y_{11}$ and $Y_{12}$ is an alkylene group having 1 to 10 carbon atoms, which may be the same as or different from each other, and each $R_{11}$ and $R_{12}$ is a hydrogen atom, alkyl group having 1 to 10 carbon atoms, alkoxy group having 1 to 10 carbon atoms or sulfonate group, which may be the same as or different from each other.)

Indocyanine green is excited by undergoing irradiation with near infrared light within a wavelength region of 760 nm to 780 nm and emits near infrared fluorescence within a wavelength region of 800 nm to 850 nm. In addition, indocyanine green has low toxicity and is detoxified through decomposition in a living body. Furthermore, because indocyanine green is water-soluble and is not accumulated in but discharged from a living body, the safety has been confirmed. Accordingly, indocyanine green has been conventionally widely used for medical practice such as liver function test and circulatory function test.

When indocyanine green is used as the fluorescent dye and a polyurethane urea resin is used as the urethane resin, a negative charge due to a sulfonic acid group of the indocyanine green and a positive charge due to an amino group in the urethane resin form an intramolecular salt. As a result, the ionicity of the whole molecule of indocyanine green decreases and the water solubility is suppressed. Accordingly, indocyanine green is remarkably suppressed from dissolving into an aqueous phase. In addition, molecules of indocyanine green are also suppressed from being aggregated to each other, and are easy to uniformly disperse in the polyurethane urea resin, so that it is possible to observe higher-luminance fluorescence upon irradiation with near infrared light. Sodium iodide may be added to indocyanine green at a concentration of, for example, 5% or less, similarly to indocyanine green used for medical use.

Publicly known derivatives of indocyanine green can be used, and examples thereof are not particularly limited, but can include ones having a substituent introduced such as an alkyl group, aryl group, sulfonic acid group and alkoxy group.

(3) Others

The fluorescent resin composition according to the present invention may contain additives such as an antioxidant, coloring agent and antibacterial agent, as required.

As described above, according to the fluorescent resin composition of the present invention, the fluorescent dye is so rigidly enclosed in the urethane resin that the fluorescent dye can be suppressed from dissolving into an aqueous phase. In addition, the fluorescent resin composition according to the present invention is excellent in compatibility and adhesiveness to a base material such as metal by containing the urethane resin as described above, and also allows for hydrophilic coating process.

2. Method for Producing Fluorescent Resin Composition

Hereinafter, a description is made of a method for producing the fluorescent resin composition according to the present invention. The fluorescent resin composition of the present invention can be obtained by adding the fluorescent dye to a solution of the urethane resin dissolved in a solvent. As the solvent, organic solvents having a low boiling point can be used, and examples thereof include methyl ethyl ketone, acetone, isopropanol, ethanol, diacetone alcohol, ethyl acetate and tetrahydrofuran. One kind of these solvents may be used alone, or two or more kinds thereof may be used in combination, but from the viewpoint of viscosity stability, it is more preferable to use two or more kinds thereof in combination.

The urethane resin is obtained by polymerizing at least the polyol compound (A) and the polyisocyanate compound (B). More specifically, first, the polyol compound (A), polyisocyanate compound (B) and chain-extending compound (C) are mixed, stirred and reacted, followed by addition of the solvent to prepare a solution of polyurethane resin (prepolymer solution).

When the silane coupling compound (D) is contained in the urethane resin, a solution obtained by previously dissolving the silane coupling compound (D) in a solvent is added to the above-described prepolymer solution under stirring.

When the urethane resin is the polyurethane urea resin, a solution obtained by previously dissolving the diamine compound (C1) in a solvent may be added to the above-described prepolymer solution under stirring and reacted to prepare a solution of polyurethane urea resin.

The solvent for dissolving the chain-extending compound (C) or silane coupling compound (D) may be the same as or different from the solvent used in the step of preparing the solution of polyurethane resin (prepolymer solution) described above. From the viewpoint of viscosity stability of the solution, two or more solvents may be mixed for use.

In the step of producing the urethane resin, the charged amount of each component constituting the urethane resin can be appropriately determined depending on the molar ratio of each structural unit or structural component in the urethane resin after polymerization. The ratio of charged amount of the polyol compound (A) to the polyisocyanate compound (B) is usually within a range of 1:2 to 1:8 in molar ratio, preferably within a range of 1:2 to 1:6. It is not preferable that the molar ratio is 1:2 or more because the dissolution property of the fluorescent dye becomes larger, and the molar ratio is 1:8 or less because the solution stability of the urethane resin deteriorates and the dispersibility of the fluorescent dye decreases. In addition, the molar ratio of the polyol compound (A), polyisocyanate compound (B) and chain-extending compound (C) preferably satisfies C/(B−A)>1.0. Furthermore, when the urethane resin includes the silane coupling compound (D), the molar ratio of the polyol compound (A), polyisocyanate compound (B), chain-extending compound (C) and silane coupling compound (D) preferably satisfies C/(B−A−D)>1.0.

The reaction temperature is usually within a range of 10 to 200° C., preferably within a range of 50 to 150° C., although the polymerization reaction depends on the type of compound used, condition for the used catalyst or the like. The reaction time is usually within a range of 10 minutes to 24 hours, preferably within a range of 1 to 10 hours.

A solution of the fluorescent resin composition according to the present invention can be obtained by adding the fluorescent dye to the solution of urethane resin obtained as described above. The fluorescent resin composition is obtained by drying this solution of the fluorescent resin composition to remove the solvent.

Both the urethane resin and the fluorescent dye are soluble in the above-described low-boiling-point solvent, so that the coating processability in a solution state is excellent. In addition, even when the solvent volatilizes, the compatibility between the urethane resin and the fluorescent dye is so excellent that the fluorescent dye is in a uniformly dispersed state in the urethane resin. Therefore, when irradiated with near infrared light, higher-luminance near infrared fluorescence can be observed.

3. Molded Object

The fluorescent resin composition according to the present invention can be used as it is as a coating agent, adhesive, paint or the like. Furthermore, the fluorescent resin composition according to the present invention can be formed into a molded object through appropriate molding. The molded object is not particularly limited for its application, but is applicable to a wide range of fields, for example, materials such as film, fiber, tube and net, shoes and bags, household electric appliances, mobile electric devices, and parts and products of moving bodies and the like such as vehicle such as automobile and motorcycle, ship and aircraft. The molded object can be produced by molding the fluorescent resin composition using a publicly known method, examples of the method including a casting method, molding method, slab molding method and laminate molding method. The molded object can be shaped by, for example, a method for forming the fluorescent resin composition into a desired shape, followed by drying.

4. Medical Device

The fluorescent resin composition according to the present invention is excellent in compatibility and adhesiveness to a base material such as metal, and also allows for hydrophilic coating process, so that it can be applied to, for example, medical devices. When the fluorescent resin composition is subjected to hydrophilic coating process, the lubricity in an aqueous phase is improved, so that even when the medical device is inserted into a living body, the lubricity in a living body is good, and also the fluorescent dye does not dissolve into blood or lymph. Accordingly, it can be safely used.

In particular, the fluorescent dye of the present invention has a property of fluorescing with near infrared light within a wavelength region of 700 nm to 1300 nm, but the near infrared light within this wavelength region is easily transmitted through the living body. Therefore, the fluorescent resin composition of the present invention can be suitably used as a position detection marker particularly for a medical device to be introduced or indwelled in a living body. Examples of the medical device can include medical wires such as lymphatic vessel wire and guide wire for treatment of lymphedema; inserting devices such as sheath introducer and dilator; catheters such as for ureter, bile duct, heart and brain; tubes such as drain tube and shunt tube; needles such as injection needle, puncture needle and biopsy needle; prostheses such as stent and stent graft; and coil emboli.

Although the fluorescent dye such as indocyanine green is a compound exhibiting water solubility, it is enclosed in the fluorescent resin composition. Accordingly, even in a surgical treatment including inserting the medical device such as medical wire into the patient's body, the fluorescent dye hardly dissolves into blood or lymph in the body. Furthermore, the dispersibility of the fluorescent dye in the urethane resin is so excellent that fluorescence upon irradiation with near infrared light can be confirmed with higher-luminance, which makes it easy to discriminate the position of the medical device in the body, and thus possible to greatly shorten the treatment time.

<Wire for Detecting Position of Lymph Vessel>

The medical device of the present invention can include various types of medical wires, in particular wires for detecting the position of lymph vessel. Lymphedema that occurs after treatment for breast cancer or uterine cancer is caused by obstruction in the center of lymph, and the inner diameter of lymph vessel is as thin as 0.2 mm to 0.5 mm. Accordingly, when performing lymphatico-venous anastomosis etc., it is necessary to accurately confirm an optimal lymph vessel for anastomosis and a vein near it. The fluorescent resin composition of the present invention fluoresces with near infrared light which is hardly absorbed by a living body. Accordingly, using the composition for a wire for detecting the position of lymph vessel allows the wire for detecting the position of lymph vessel to fluorescent inside a lymph vessel, thereby accurately ascertaining the positions of the lymph vessel and vein. As a result, it is possible to identify an optimal part for anastomotic site and shorten the operation time. Furthermore, in the present invention, it is possible to confirm the position of lymph vessel or blood vessel without using X-rays, thereby eliminating exposure of the patient.

Figure 1B:
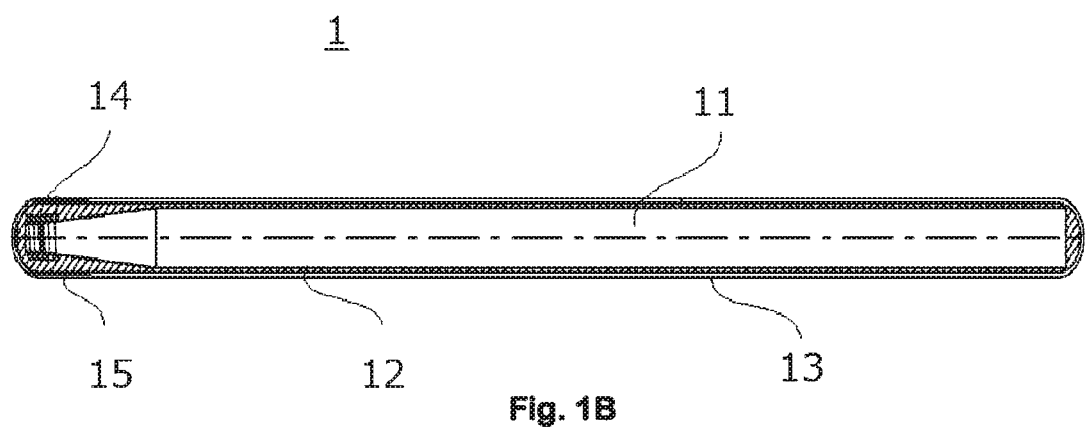
FIG. 1B is a schematic cross-sectional view of a wire for detecting the position of a lymph vessel according to one embodiment of the present invention.

Hereinafter, with reference to FIGS. 1A-2B, a description is made of a medical wire (wire for detecting the position of lymph vessel) using the fluorescent resin composition according to the present invention. FIGS. 1A and 1B are schematic views showing the wire for detecting the position of lymph vessel according to one embodiment of the present invention, in which FIG. 1A is a side view and FIG. 1B is a schematic cross-sectional view. The shape, length, diameter, thickness, dimensional ratio and the like of each structure of the wire for detecting the position of lymph vessel 1 are schematically shown, and thus they may be different from those of an actually used wire for detecting the position of lymph vessel.

As shown in FIG. 1A, the wire for detecting the position of lymph vessel 1 of the present embodiment is provided with a marker portion 15. In addition, as shown in FIG. 1B, the wire for detecting the position of lymph vessel 1 includes a core wire portion 11, tube covering portion 12 and hydrophilic coating portion 13. The outer diameter of the wire for detecting the position of lymph vessel 1 has a thickness that allows for insertion into a lymph vessel of a living body, preferably of 0.1 mm to 0.5 mm.

The core wire portion 11 constitutes the center portion of the wire for detecting the position of lymph vessel 1, at least one end portion of which has a tapered shape that tapers toward the distal end. The length of the core wire portion 11 is not particularly limited, but, for example, 700 mm to 2500 mm. A material used for the core wire portion 11 is not limited, but, for example, an Ni/Ti alloy or stainless steel is preferably used.

In addition, as shown in FIG. 1B, an X-ray contrast agent portion 14 may be provided at the distal end of the tapered portion of the core wire portion 11. The X-ray contrast agent portion 14 is preferably composed of a metal such as a platinum alloy, tungsten or gold so as to allow for X-ray imaging. The X-ray contrast agent portion 14 has a length of 5 mm to 80 mm, for example. Although the X-ray contrast agent portion 14 has a coil shape as shown in FIGS. 1A and 1B, the shape is not limited thereto, but may be modified as appropriate.

The tube covering portion 12 is provided so as to cover the core wire portion 11 and the X-ray contrast agent portion 14. As the tube covering portion 12, for example, a polyamide resin, polyurethane resin, vinyl chloride, polyolefin or the like is preferably used. In addition, as the material of the tube covering portion 12, the urethane resin according to the present invention can be used.

The hydrophilic coating portion 13 is provided so as to cover the outer peripheral surface of the tube covering portion 12. The hydrophilic coating portion 13 can be formed by adopting a conventionally generally adopted method such as a method including immersing the wire for detecting the position of lymph vessel 1 provided with the tube covering portion 12 around the core wire portion 11 and the X-ray contrast agent portion 14 in a solution of hydrophilic polymer, or a method including applying or spraying a solution of hydrophilic polymer.

The hydrophilic polymer used for the hydrophilic coating portion 13 is not limited, but, for example, a maleic anhydride copolymer compound, polyvinyl pyrrolidone, dimethyl acrylamide copolymer, polyacrylamide, hyaluronic acid and polyethylene glycol may be used.

As a solvent used for preparing a solution of the above-described hydrophilic polymer, a general organic solvent, for example, a ketone solvent such as acetone or methyl ethyl ketone, an alcohol solvent such as methanol, ethanol or isopropanol, tetrahydrofuran, or a mixed solvent thereof may be used. A hydrophilic polymer is dissolved in such a solvent so as to have a concentration of 1 wt % to 15 wt %, preferably 2 wt % to 8 wt % to prepare the solution of the hydrophilic polymer.

A part of the wire for detecting the position of lymph vessel 1 may be provided with the marker portion 15 composed of the fluorescent resin composition according to the present invention. The marker portion 15 is preferably provided at the distal end portion of the wire for detecting the position of lymph vessel 1 so that the insertion position and the insertion distance of the wire can be clearly determined. From the viewpoints of ease observation of fluorescence and lubricity of the wire for detecting the position of lymph vessel 1, the marker portion 15 is preferably provided outside the tube covering portion 12 and inside the hydrophilic coating portion 13. After the tube covering portion 12 is formed, the marker portion 15 can be obtained by applying a solution in which the fluorescent resin composition according to the present invention is dissolved in the organic solvent, followed by drying to remove the organic solvent.

As described above, the wire for detecting the position of lymph vessel 1 having the marker portion 15 composed of the fluorescent resin composition according to the present invention prevents the fluorescent dye from dissolving into blood or lymph when inserted into a living body. In addition, irradiation with near infrared light allows for observation of higher-luminance fluorescence, so that the position of the wire for detecting the position of lymph vessel 1 is easily confirmed.

Figure 2A:
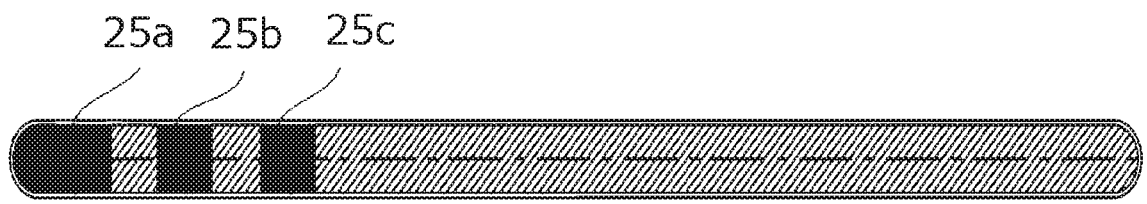
FIG. 2A is a schematic view showing a wire for detecting the position of a lymph vessel according to another embodiment of the present invention in which the marker portions are provided at three locations on the distal end side.
Figure 2B:
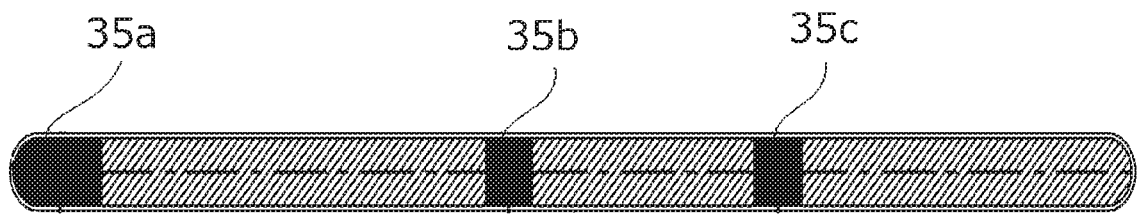
FIG. 2B is a schematic view showing a wire for detecting the position of a lymph vessel according to another embodiment of the present invention in which the marker portions are provided at one location on the distal end side and two locations in the intermediate portion.

FIGS. 2A and 2B are schematic views showing the wire for detecting the position of lymph vessel according to another embodiment of the present invention. The marker portion 15 may be provided at only one location of the wire for detecting the position of lymph vessel 1 as shown in FIGS. 1A and 1B, but it is preferable that the marker portions are provided in a certain part and at a plurality of locations thereof. The wire for detecting the position of lymph vessel 2 shown in FIG. 2A shows an embodiment in which the marker portions 25a to 25c are provided at three locations on the distal end side. In this way, the marker portions 25a to 25c are provided at a plurality of locations on the distal end side of the wire for detecting the position of lymph vessel 2, which makes it easier to confirm the position on the distal end side, and also makes it possible to measure the distance based on intervals among the marker portions 25a to 25c.

Furthermore, the wire for detecting the position of lymph vessel 3 shown in FIG. 2B shows an embodiment in which the marker portions 35a to 35c are provided at one location on the distal end side and two locations in the intermediate portion. In this way, the marker portions 35a to 35c are provided also in the intermediate portion of the wire for detecting the position of lymph vessel 3, which makes it possible to ascertain not only the position on the distal end side but also the position in the intermediate portion.

EXAMPLES

Hereinafter, a specific description is made of the present invention with reference to Examples, but these Examples do not limit an object of the present invention. In the following Examples, the "%" indication is on a mass basis (mass percent) unless otherwise specified.

Example 1

(Manufacture of Molded Object (Film))
In a 500 mL three-necked flask, 0.02 mol (40 g) of aliphatic polycarbonate diol having a number average molecular weight of 2000 (polycarbonate diol synthesized from 1,6-hexanediol and diphenyl carbonate (Desmophen (Registered Trademark) 2020E, made by Sumitomo Bayer Co., Ltd.)) and 0.08 mol (17.76 g) of isophorone diisocyanate were charged and reacted under stirring at 110° C. for 3 hours, then cooled, and 176 g of dehydrated methyl ethyl ketone was charged to prepare a homogeneous prepolymer solution. Then, a solution obtained by dissolving 0.065 mol (11.05 g) of isophorone diamine in 43 g of dehydrated isopropanol was added to the above-described prepolymer solution under stirring, and the reaction was continued for 30 minutes. In this way, a solution of a polyurethane urea resin (1) having an amino group in the molecule was obtained.

In the obtained solution of the polyurethane urea resin (1), 30 mg of indocyanine green (ICG) with respect to 1 g of the resin in terms of solid content was added to prepare a solution of an ICG composite resin composition. The solution of the ICG composite resin composition was cast and dried at 80° C. for 1 hour to prepare a film.

(Dissolution Test of ICG from Film)

A film section of 3 cm×3 cm×50 μm was cut out from the film, and one piece of the film section was immersed and then left to stand in 50 mL of water at room temperature for 1 day. Subsequently, the immersed film section was removed, and the remaining aqueous solution was used as a sample solution.

(Preparation of Standard Solution)

Indocyanine green (ICG) was dissolved in water according to the following concentrations to prepare 10 kinds of standard solutions. The degree of dissolved amount of ICG from the film section was evaluated in 10 grades by comparing the color density of the standard solutions with the color density of the sample solution. Furthermore, the dispersibility of ICG and the presence or absence of bleed out of ICG were confirmed by visually recognizing the film. The evaluation results are shown in Table 1.

(Concentration of ICG Aqueous Solution of Standard Solution and 10-Grade Evaluation of Color Intensity in Sample Solution)

ICG 10 mg/L . . . 10
ICG 8 mg/L . . . 9
ICG 6 mg/L . . . 8
ICG 4 mg/L . . . 7
ICG 2 mg/L . . . 6
ICG 1 mg/L . . . 5
ICG 0.5 mg/L . . . 4
ICG 0.3 mg/L . . . 3
ICG 0.1 mg/L . . . 2
ICG 0.0 mg/L . . . 1

As shown in Table 1, the color density of the sample solution according to Example 1 was 1 to 2 in the above-described 10-grade evaluation, which indicated that the sample solution was almost colorless and transparent, and almost no dissolution of ICG into water was observed. This shows that ICG was rigidly enclosed in the polyurethane urea resin (1). In addition, the film according to Example 1 exhibited a transparent green color, and had ICG uniformly dispersed.

Example 2

In a 500 mL three-necked flask, 0.02 mol (40 g) of aliphatic polycarbonate diol having a number average molecular weight of 2000 (Nipporane (registered trademark) 982R, made by Tosoh Corporation) and 0.08 mol (17.76 g) of isophorone diisocyanate were charged and reacted under stirring at 110° C. for 3 hours, then cooled, and 180 g of dehydrated methyl ethyl ketone was charged to prepare a homogeneous prepolymer solution. Then, a solution obtained by dissolving 0.049 mol (8.33 g) of isophorone diamine in 50 g of dehydrated isopropanol, and a solution obtained by dissolving 0.01 mol (2.064 g) of 3-(2-aminoethyl) aminopropylmethyldimethoxysilane and 0.01 mol (1.79 g) of 3-aminopropyltrimethoxysilane in 50 g of dehydrated isopropanol were sequentially added to the above-described prepolymer solution under stirring, and the reaction was continued for 30 minutes. In this way, a solution of a polyurethane urea resin (2) having an amino group in the molecule was obtained.

Also regarding the polyurethane urea resin (2), in the same manner as in Example 1, a film of an ICG composite resin composition and a sample solution were prepared and evaluated, and the results are shown in Table 1. As shown in Table 1, the color density of the sample solution according to Example 2 was 1 in the above-described 10-grade evaluation, which indicated that no dissolution of ICG into water was observed at all. This shows that ICG was completely enclosed in the polyurethane urea resin (2).

In addition, the film of the ICG composite resin composition according to Example 2 exhibited a transparent green color, and had ICG uniformly dispersed.

Example 3

In a 500 mL three-necked flask, 0.02 mol (40 g) of aliphatic polycarbonate diol having a number average molecular weight of 2000 (polycarbonate diol synthesized from 1,6-hexanediol and diphenyl carbonate (Desmophen (Registered Trademark) 2020E, made by Sumitomo Bayer Co., Ltd.)), 0.04 mol (10 g) of 4,4'-diphenylmethane diisocyanate, 0.022 mol (1.98 g) of 1,4-butanediol and 200 g of dehydrated tetrahydrofuran were charged and reacted under stirring at 60° C. for 10 hours, then cooled to prepare a solution of polyurethane resin (3).

Also regarding the polyurethane resin (3), in the same manner as in Example 1, a film of an ICG composite resin composition and a sample solution were prepared and evaluated, and the results are shown in Table 1. As shown in Table 1, the color density of the sample solution according to Example 3 was 2 to 3 in the above-described 10-grade evaluation, which indicated that dissolution of ICG into water was very slight. This shows that ICG was enclosed in the polyurethane resin (3).

In addition, the film of the ICG composite resin composition according to Example 3 exhibited a transparent green color, and had ICG substantially uniformly dispersed.

Comparative Example 1

In a 500 mL three-necked flask, 0.02 mol (40 g) of polytetramethylene ether glycol having a number average molecular weight of 2000 and 0.08 mol (17.76 g) of isophorone diisocyanate were charged and reacted under stirring at 110° C. for 3 hours, then cooled, and 176 g of dehydrated methyl ethyl ketone was charged to prepare a homogeneous prepolymer solution. Then, a solution obtained by dissolving 0.065 mol (11.05 g) of isophorone diamine in 43 g of dehydrated isopropanol was added to the above-described prepolymer solution under stirring, and the reaction was continued for 30 minutes. In this way, a solution of a polyurethane urea resin (4) having an amino group in the molecule was obtained.

Also regarding the polyurethane urea resin (4), in the same manner as in Example 1, a film of an ICG composite resin composition and a sample solution were prepared and evaluated, and the results are shown in Table 1. As shown in Table 1, the color density of the sample solution according to Comparative Example 1 was 10 in the above-described 10-grade evaluation, which indicated that dissolution of ICG into water was very large. This shows that the polyurethane urea resin (4) had very poor enclosing effect on ICG.

In addition, the film of the ICG composite resin composition according to Comparative Example 1 was discolored to a brown color, and had a portion where ICG was aggregated.

Comparative Example 2

In a 500 mL three-necked flask, 0.02 mol (40 g) of polytetramethylene ether glycol having a number average molecular weight of 2000, 0.04 mol (10 g) of 4,4'-diphenylmethane diisocyanate, 0.022 mol (1.98 g) of 1,4-butanediol and 200 g of dehydrated tetrahydrofuran were charged, reacted under stirring at 60° C. for 10 hours, and then cooled to prepare a solution of a polyurethane resin (5).

Also regarding the polyurethane resin (5) according to Comparative Example 2, in the same manner as in Example 1, a film of an ICG composite resin composition and a sample solution were prepared and evaluated, and the results are shown in Table 1. As shown in Table 1, the color density of the sample solution according to Comparative Example 2 was 9 in the above-described 10-grade evaluation, which indicated that dissolution of ICG into water was very large. This shows that the polyurethane resin (5) had poor enclosing effect on ICG.

In addition, the film of the ICG composite resin composition according to Comparative Example 2 was discolored to a brown color, and had a portion where ICG was aggregated. Furthermore, ICG resulted in bleed out.

Comparative Example 3

In a 500 mL three-necked flask, 0.02 mol (40 g) of polybutylene adipate glycol having a number average molecular weight of 2000, 0.04 mol (10 g) of diphenylmethane diisocyanate, 0.022 mol (1.98 g) of 1,4-butanediol and 200 g of dehydrated tetrahydrofuran were charged, reacted under stirring at 60° C. for 10 hours, and then cooled to prepare a solution of a polyurethane resin (6).

Also regarding the polyurethane resin (6) according to Comparative Example 3, in the same manner as in Example 1, a film of an ICG composite resin composition and a sample solution were prepared and evaluated, and the results are shown in Table 1. As shown in Table 1, the color density of the sample solution according to Comparative Example 3 was 8 in the above-described 10-grade evaluation, which indicated that dissolution of ICG into water was very large. This shows that the polyurethane resin (6) had poor enclosing effect on ICG.

In addition, the film of the ICG composite resin composition according to Comparative Example 3 had no observed discoloration, but had a portion where ICG was aggregated. Furthermore, ICG resulted in bleed out.

TABLE 1

|  | EXAMPLE 1 | EXAMPLE 2 | EXAMPLE 3 | COMPARATIVE EXAMPLE 1 |
|---|---|---|---|---|
| RESIN | POLYURETHANE UREA RESIN (1) | POLYURETHANE UREA RESIN (2) | POLYURETHANE RESIN (3) | POLYURETHANE UREA RESIN (4) |
| POLYOL COMPOUND (A) | ALIPHATIC POLYCARBONATE DIOL | ALIPHATIC POLYCARBONATE DIOL | ALIPHATIC POLYCARBONATE DIOL | POLYTETRAMETHYLENE ETHER GLYCOL |
| POLYISOCYANATE COMPOUND (B) | ISOPHORONE DIISOCYANATE | ISOPHORONE DIISOCYANATE | DIPHENYLMETHANE DIISOCYANATE | ISOPHORONE DIISOCYANATE |
| CHAIN-EXTENDING COMPOUND (C): DIAMINE COMPOUND (C1) | ISOPHORONE DIAMINE | ISOPHORONE DIAMINE |  | ISOPHORONE DIAMINE |
| CHAIN-EXTENDING COMPOUND (C): DIOL COMPOUND (C2) |  |  | 1,4-BUTANEDIOL |  |
| SILANE COUPLING COMPOUND (D) | − | + | − | − |
| DISSOLVED AMOUNT OF ICG | 1-2 | 1 | 2-3 | 10 |
| DISPERSIBILITY OF ICG | NO AGGREGATES EXIST | NO AGGREGATES EXIST | VERY FEW AGGREGATES EXIST | AGGREGATES EXIST |
| BLEED OUT OF ICG | — | — | — | — |

TABLE 1-continued

|  | | COMPARATIVE EXAMPLE 2 | COMPARATIVE EXAMPLE 3 |
|---|---|---|---|
| | RESIN | POLYURETHANE RESIN (5) | POLYURETHANE RESIN (6) |
| | POLYOL COMPOUND (A) | POLYTETRAMETHYLENE ETHER GLYCOL | POLYBUTYLENE ADIPATE GLYCOL |
| | POLYISOCYANATE COMPOUND (B) | DIPHENYLMETHANE DIISOCYANATE | DIPHENYLMETHANE DIISOCYANATE |
| | CHAIN-EXTENDING COMPOUND (C): DIAMINE COMPOUND (C1) | | |
| | CHAIN-EXTENDING COMPOUND (C): DIOL COMPOUND (C2) | 1,4-BUTANEDIOL | 1,4-BUTANEDIOL |
| | SILANE COUPLING COMPOUND (D) | – | – |
| | DISSOLVED AMOUNT OF ICG | 9 | 8 |
| | DISPERSIBILITY OF ICG | AGGREGATES EXIST | AGGREGATES EXIST |
| | BLEED OUT OF ICG | BLEED OUT | BLEED OUT |

Example 4

(Manufacture of Wire for Detecting Position of Lymph Vessel)

In order to perform a hydrophilic coating process, a wire manufactured in this manner was immersed in a 3% solution of methyl vinyl ether-maleic anhydride copolymer compound (GANTREZ (registered trademark) AN-169 made by IPS), pulled up at a speed of 3 cm/sec, air-dried, and then dried at 100° C. for 60 minutes for fixing on the surface. Thereafter, the wire was immersed in a 1/10 N aqueous solution of sodium hydroxide to be treated at room temperature for 30 minutes. Furthermore, the wire was sufficiently washed with water and then dried at 60° C. for 30 minutes to prepare a wire for detecting the position of lymph vessel.

The wire for detecting the position of lymph vessel obtained by the above-described method exhibited excellent lubricity and lubrication durability in physiological saline, and no dissolution of indocyanine green was observed. In particular, the lubricity and lubrication durability of the marker portion were very good, and the lubrication performance was not different from that in any other portion of the wire but excellent.

(Test Using Domestic Pig)

An animal experiment using domestic pig was performed using the wire for detecting the position of lymph vessel manufactured in above Example 4. The epidermis of the left lower leg of a domestic pig (weight 50 kg) was incised and a sheath was firstly introduced through the vein to the inguinal region. Next, the wire for detecting the position of lymph vessel was inserted through the proximal end of the sheath into a lumen, and extended from the distal end of the sheath to advance into the lymph vessel. The operation was performed while confirming the fluorescence from the marker portion by irradiating the wire for detecting the position of lymph vessel with near infrared rays using an infrared camera system (pde-neo (registered trademark) infrared observation camera system C 10935-20 made by Hamamatsu Photonics KK). As a result, it was possible to deeply visualize the travel from the upper site of the knee to a deep part of the inguinal region of the domestic pig.

Figure 3A:
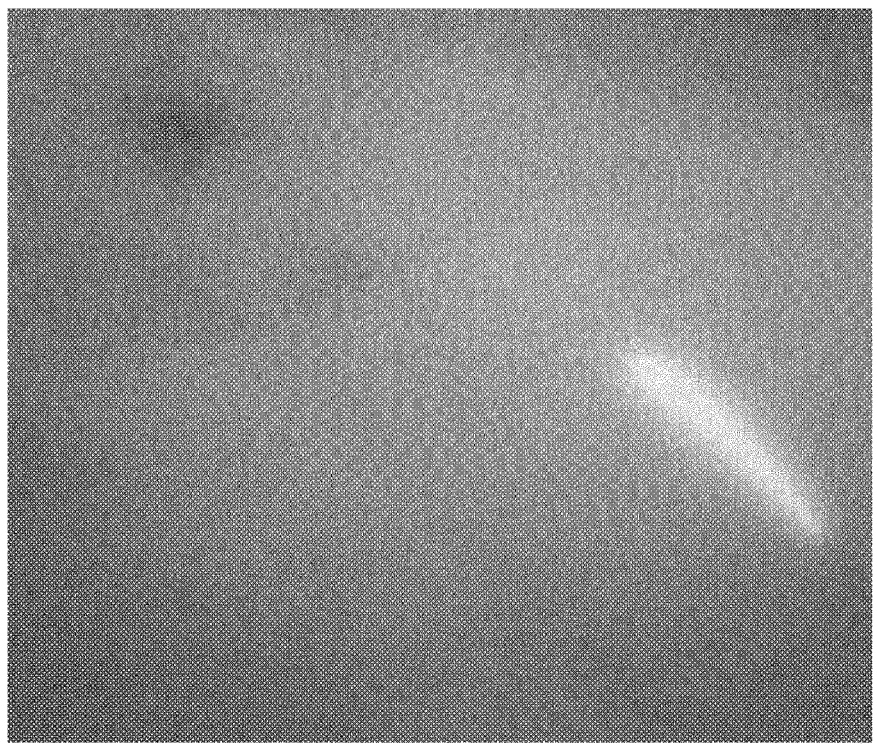
FIG. 3A is a photograph showing a state of fluorescence when a wire for detecting the position of a lymph vessel according to Example 4 is inserted into a domestic pig body and irradiated with near infrared light and the fluorescent portion is in a straight portion of the vessel.
Figure 3B:
FIG. 3B is a photograph showing a state of fluorescence when a wire for detecting the portion of a lymph vessel according to Example 4 is inserted into a domestic pig body and irradiated with near infrared light and the fluorescent portion is in a curved portion of the vessel.

FIGS. 3A and 3B show how the marker portion of the wire for detecting the position of lymph vessel travels in a lymph vessel. As shown in FIGS. 3A and 3B, it can be seen that the marker portion (fluorescent portion) travels in the lymph vessel as the wire for detecting the position of lymph vessel advances. In addition, in FIG. 3B, because the fluorescent portion draws a curve, it can be confirmed that the marker portion travels the bending part of the lymph vessel.

As described above, the insertion position of the wire for detecting the position of lymph vessel is clarified in the body, so that a surgical treatment such as lymphatico-venous anastomosis using microsurgery to cause a lymph vessel to be anastomosed to a subcutaneous vein to flow lymph into the vein can be performed more effectively than before.

REFERENCE SIGNS LIST 1 to 3 Wire for detecting the position of lymph vessel
11 Core wire portion
12 Tube covering portion
13 Hydrophilic coating portion
14 X-ray contrast agent portion
15, 25a to 25c, 35a to 35c Marker portion

[Formula 3]
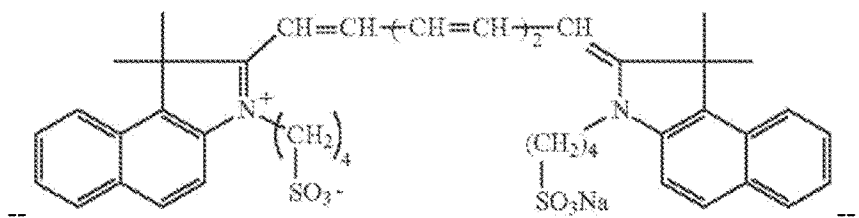

The invention claimed is:

1. A fluorescent resin composition comprising a urethane resin which is a polymer having at least a polyol compound (A), a polyisocyanate compound (B) and a chain-extending compound (C) as structural units, and a fluorescent dye that emits fluorescence by undergoing irradiation with near infrared light within a wavelength region of 700 nm to 1300 nm, the polyol compound (A) being an aliphatic polycarbonate diol (A1), the fluorescent dye being a cyanine dye that emits fluorescence by undergoing irradiation with near infrared light within a wavelength region of 700 nm to 900 nm, and the cyanine dye being indocyanine green represented by following Formula (1) or a derivative of indocyanine green represented by following Formula (2),

[Formula 1]

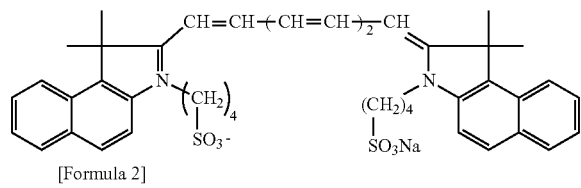

[Formula 2]

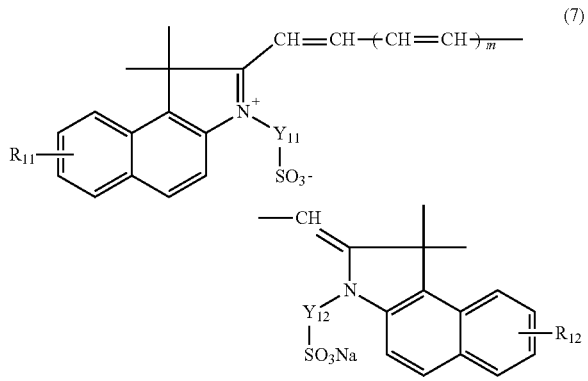

wherein, m is an integer of 1 to 3, each $Y_{11}$ and $Y_{12}$ is an alkylene group having 1 to 10 carbon atoms, which may be the same or different from each other, and each $R_{11}$ and $R_{12}$ is a hydrogen atom, an alkyl group having 1 to 10 carbon atoms, an alkoxy group having 1 to 10 carbon atoms or a sulfonate group, which may be the same or different from each other.

2. The fluorescent resin composition according to claim 1, wherein the polyol compound (A) has a number average molecular weight within a range of 500 to 5000.

3. The fluorescent resin composition according to claim 1, wherein the polyisocyanate compound (B) is one or more selected from an alicyclic diisocyanate (B1), aliphatic diisocyanate (B2) and aromatic diisocyanate (B3).

4. The fluorescent resin composition according to claim 1, wherein the urethane resin is a urethane urea resin, and the chain-extending compound (C) further contains one or more diamine compounds (C1) selected from an alicyclic diamine (C1-1) and aliphatic diamine (C1-2) as a structural unit.

5. The fluorescent resin composition according to claim 4, wherein a molar ratio of the polyol compound (A), the polyisocyanate compound (B) and the chain-extending compound (C) constituting the urethane resin satisfies C/(B-A) >1.0.

6. The fluorescent resin composition according to claim 1, wherein the urethane resin is bonded to a silane coupling compound (D) having an amino group.

7. The fluorescent resin composition according to claim 6, wherein a molar ratio of the polyol compound (A), the polyisocyanate compound (B), the chain-extending compound (C) and the silane coupling compound (D) constituting the urethane resin satisfies C/(B-A-D) >1.0.

8. A molded object comprising the fluorescent resin composition according to claim 1.

9. A medical device comprising the molded object according to claim 8.

10. The medical device according to claim 9, wherein the medical device is a medical wire comprising the molded object as a fluorescent marker.

11. A method for producing a fluorescent resin composition, the method comprising:
a solution preparing step of polymerizing at least a polyol compound (A), a polyisocyanate compound (B) and a chain-extending compound (C) in the presence of a solvent to prepare a solution of a urethane resin; and
a dye mixing step of mixing a fluorescent dye that emits fluorescence by undergoing irradiation with near infrared light within a wavelength region of 700 nm to 1300 nm with the solution of the urethane resin,
the polyol compound (A) being an aliphatic polycarbonate diol (A1),
the fluorescent dye being a cyanine dye that emits fluorescence by undergoing irradiation with near infrared light within a wavelength region of 700 nm to 900 nm, and the cyanine dye being indocyanine green represented by following Formula (3) or a derivative of indocyanine green represented by following Formula (4),

[Formula 3]

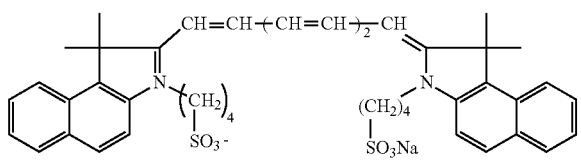

[Formula 4]

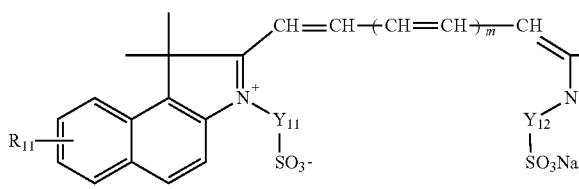

wherein, m is an integer of 1 to 3, each $Y_{11}$ and $Y_{12}$ is an alkylene group having 1 to 10 carbon atoms, which may be the same or different from each other, and each $R_{11}$ and $R_{12}$ is a hydrogen atom, an alkyl group having 1 to 10 carbon atoms, an alkoxy group having 1 to 10 carbon atoms or a sulfonate group, which may be the same or different from each other.

12. The method for producing a fluorescent resin composition according to claim 11, wherein the solution preparing step comprises:
   a step of reacting the polyol compound (A) with the polyisocyanate compound (B) to prepare a prepolymer solution; and
   a urethane polymerizing step of adding the chain-extending compound (C) to the prepolymer solution to prepare the urethane resin.

13. The method for producing a fluorescent resin composition according to claim 11, wherein the solution preparing step further comprises a step of dissolving a silane coupling compound (D) in a solvent.

* * * * *

UNITED STATES PATENT AND TRADEMARK OFFICE
CERTIFICATE OF CORRECTION

PATENT NO. : 11,365,279 B2
APPLICATION NO. : 16/308148
DATED : June 21, 2022
INVENTOR(S) : Jiro Maegawa et al.

Page 1 of 2

It is certified that error appears in the above-identified patent and that said Letters Patent is hereby corrected as shown below:

In the Claims

Column 23, Lines 2-10, Claim 1, delete " 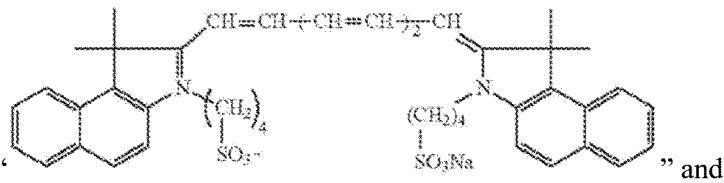 " and insert -- 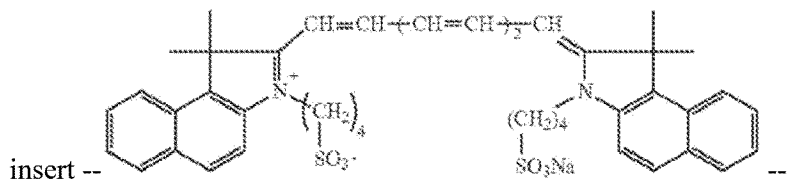 --

Columns 23-24, Lines 42-43, Claim 11, delete " 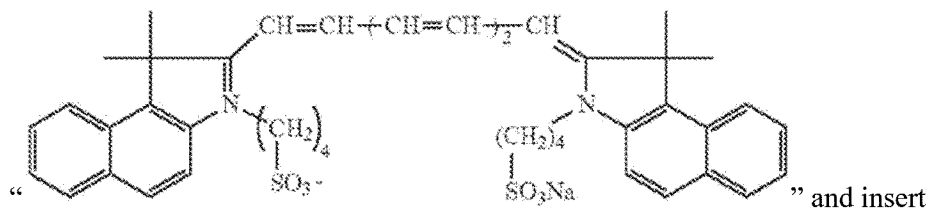 " and insert

Signed and Sealed this
Twenty-fifth Day of October, 2022

Katherine Kelly Vidal
*Director of the United States Patent and Trademark Office*